(12) United States Patent
Lilly (10) Patent No.: US 11,110,140 B1
(45) Date of Patent: Sep. 7, 2021

(54) MEDICINAL FOOD PRODUCTS AND METHODS FOR PRODUCING SAID PRODUCTS

(71) Applicant: Daniel Lilly, Crownsville, MD (US)

(72) Inventor: Daniel Lilly, Crownsville, MD (US)

(*) Notice: Subject to any disclaimer, the term of this patent is extended or adjusted under 35 U.S.C. 154(b) by 0 days.

(21) Appl. No.: 16/845,126

(22) Filed: Apr. 10, 2020

(51) Int. Cl.
*A61K 36/00* (2006.01)
*A61K 36/185* (2006.01)
*A61K 9/00* (2006.01)

(52) U.S. Cl.
CPC .......... *A61K 36/185* (2013.01); *A61K 9/0056* (2013.01)

(58) Field of Classification Search
CPC ...................................................... A61K 36/00
USPC ........................................................ 424/725
See application file for complete search history.

(56) References Cited

FOREIGN PATENT DOCUMENTS

CN 107712900 A * 2/2018

* cited by examiner

*Primary Examiner* — Michael V Meller
(74) *Attorney, Agent, or Firm* — Laubscher & Laubscher P.C.

(57) ABSTRACT

A method for producing a medicinal food product includes the steps of homogenously mixing a first non-medicinal food base with at least one medicinal product to prepare a medicinal-infused food-based carrier, adding the carrier to a second food base to prepare a medicinal-infused food item, freezing, dehydrating and dividing the food item, placing the divided items in flexible containers, and vacuum sealing the containers for prolonged storage. Preferably, the medicinal product is a cannabinoids, such as cannabis, THC, CBD, CBN or CBG.

9 Claims, 7 Drawing Sheets

MEDICINAL FOOD PRODUCTS AND METHODS FOR PRODUCING SAID PRODUCTS

BACKGROUND OF THE DISCLOSURE

The present disclosure relates generally to medicinal food products and more specifically to a medicinal-infused food item with an extended shelf life.

Ingestible medicinal products are well known in the art and are often provided via a pill or syrup, among other forms. Such items typically either do not include a flavor or have an unappetizing flavor. Recently, with the legalization of cannabis and cannabinoid products in many states of the United States, ingestible cannabinoid food products have been developed at a greater rate. Those items are provided as pills, syrups and liquids, and also as more standard food, such as candy or baked goods that include cannabinoids.

Current cannabinoid products can be unpredictable. They are typically produced in high volume and then divided into individual products to be consumed in one or a few servings. Due to the nature of preparing these products in large batches, it is difficult to prepare uniformly dosed cannabinoid products such that each divided product contains nearly identical levels of a cannabinoid compound. Further, over time, the effect of a cannabinoid compound in a food product can change, resulting in more unpredictable cannabinoid food products. Without knowing the amount and effect of a cannabinoid compound in a cannabinoid food product, consumers know little about the product he or she is buying, even if packaging lists specific levels and effects of a compound.

There is thus a need for cannabinoid food products that are more accurately and evenly dosed at the time of production, resulting in individual products that have more precise levels of a cannabinoid compound. Further, there is a need for cannabinoid products that will remain in such a precisely dosed state for an extended period of time so that users will know the level and effect of the cannabinoid compound he or she is consuming.

SUMMARY OF THE DISCLOSURE

Accordingly, it is an object of the present disclosure to provide a method for producing a medicinal food product which includes the steps of homogenously mixing a first non-medicinal food base with at least one medicinal product to prepare a medicinal-infused food-based carrier, adding the carrier to a second food base to prepare a medicinal-infused food item, sublimate by freezing and dehydrating in a vacuum, and dividing the medicinal-infused food item, and vacuum sealing the divided food item into flexible containers for prolonged storage. Preferably, the medicinal product is a cannabinoid, such as cannabis, Tetrahydrocannabinol (THC), Cannabidiol (CBD), Cannabinol (CBN) or Cannabigerol (CBG).

In one embodiment, a first non-medicinal food base and at least one cannabinoid product are mixed to prepare a first cannabinoid-infused food-based carrier. Preferably, the mixing involves heating the first cannabinoid-infused food-based carrier to between 100 and 120 degrees and sonicating the carrier.

In another embodiment, at least one additional cannabinoid product is added to the cannabinoid-infused food-based carrier after sonicating the carrier and prior to adding it to the second food base.

In yet another embodiment, an additional step includes homogenously mixing a second non-medicinal food base with at least one cannabinoid product to prepare a second cannabinoid-infused food-based carrier which is then mixed with the first carrier prior to sublimation by freezing and dehydrating in a vacuum and packaging.

It is also an object of the present disclosure to provide a medicinal food product that includes a freeze-dried medicinal food item. The food item includes a medicinal-infused food-based carrier mixed with a second food base that is then freeze-dried and vacuum sealed. The medicinal-infused food-based carrier preferably includes a homogenous mixture of first non-medicinal food base and at least one cannabinoid, such as cannabis, THC, CBD, CBN or CBG. The second food base is preferably either a non-medicinal food base or a cannabinoid-infused food base. The food product is preferably produced via equal freeze and dehydration under a vacuum for periods of approximately 10-48 hours per period prior to packaging.

BRIEF DESCRIPTION OF THE FIGURES

Other objects and advantages of the disclosure will become apparent from a study of the following specification when viewed in the light of the accompanying drawing, in which.

DETAILED DESCRIPTION

The present disclosure relates to medicinal food products in which a medicinal product is infused with at least one food base resulting in a medicinal-infused food item, which is then processed through freeze and dehydration under a vacuum for extended periods, and is vacuum sealed with oxygen absorbers in place to provide a medicinal-infused food product that is uniformly dosed and is shelf stable for a prolonged period of time.

Figure 1:
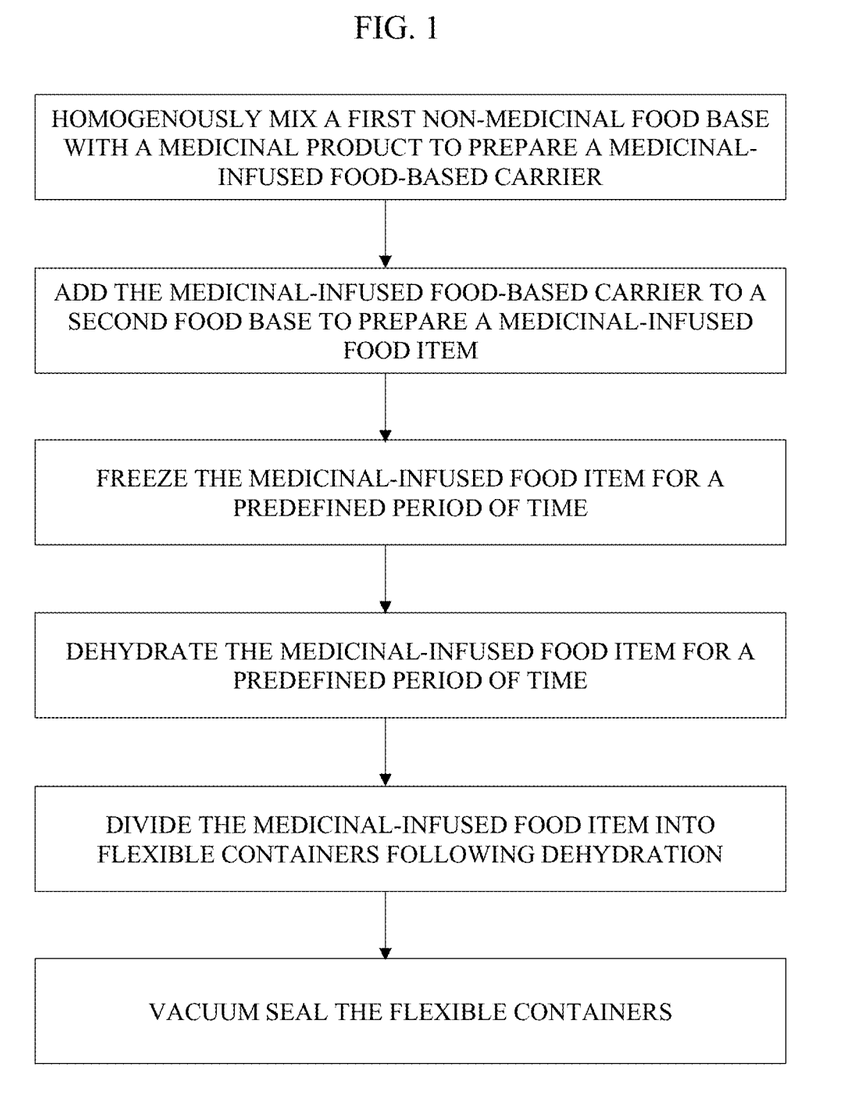
FIG. 1 is a flow chart of one method for producing a medicinal food product according to the present disclosure.

FIG. 1 shows a first method for producing such a product. A first non-medicinal food base and a medicinal product are homogenously mixed to prepare a medicinal-infused food-based carrier. The non-medicinal food base is any liquid food item, such as milk, juice, stock, jelly, or other such items, and the medicinal product is preferably a liquid cannabinoid, such as a tincture that includes cannabinoids, such as cannabis, THC, CBD, CBN or CBG. Throughout this disclosure, medicinal infusion and/or medicinal products are discussed in regard to cannabinoids. It will be understood by those with skill in the art that medicinal products other than cannabinoids can be used without deviating from the spirit of the methods and products disclosed herein.

Once the medicinal-infused food-based carrier is prepared, it is added to a second food base to prepare a medicinal-infused food item. The second food base is preferably a liquid, although a solid, such as fruit, meat or vegetables could be used. The medicinal-infused food item then passes through a freeze cycle and a dehydration cycle under vacuum, is divided, and packaged for storage. The packaging includes vacuum sealed flexible bags with oxygen absorbers in place to provide a prolonged shelf life for each product.

Figure 2:
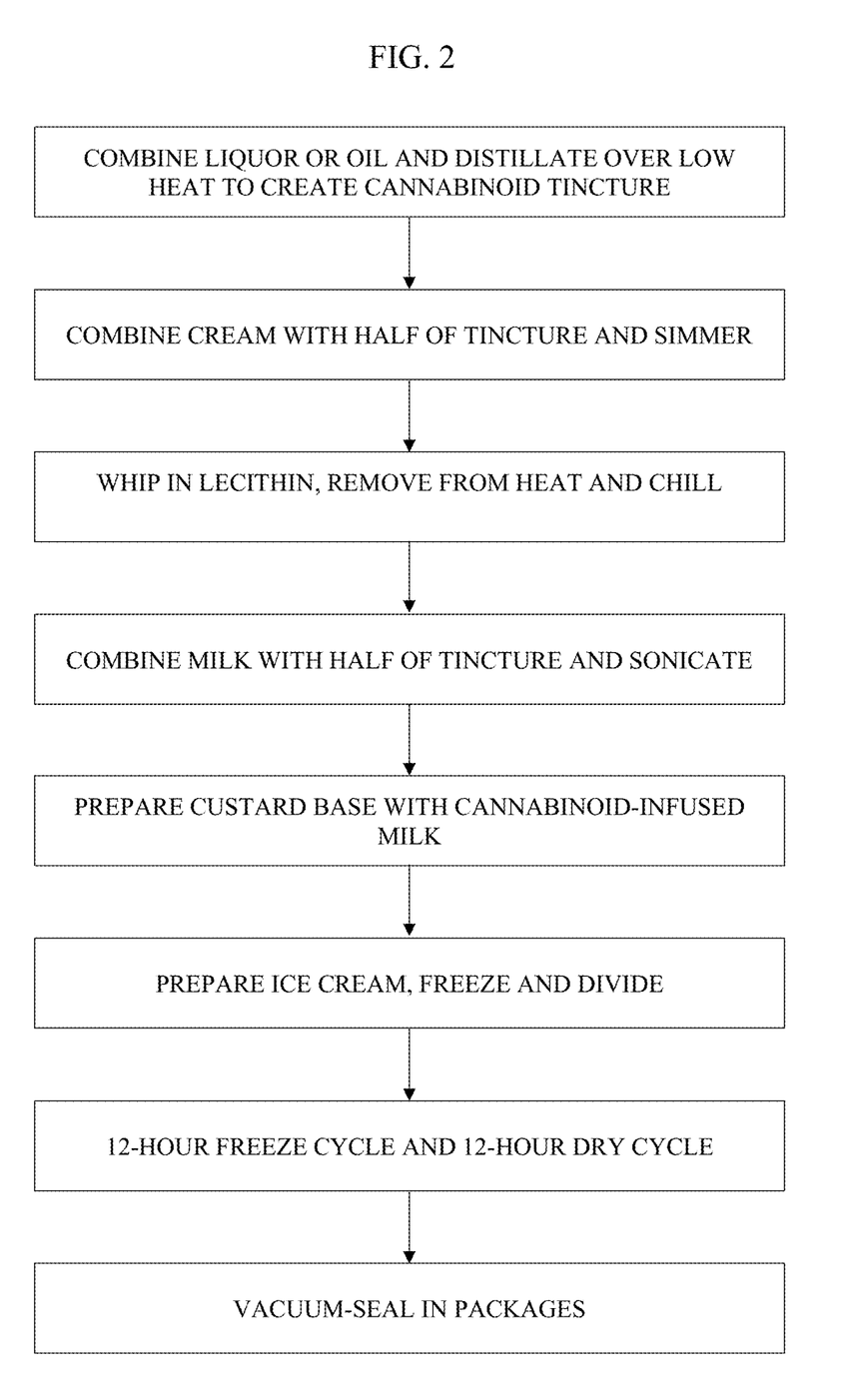
FIG. 2 is a flow chart of a second method for producing a medicinal food product according to the present disclosure.

A second method for producing a medicinal food item is shown in FIG. 2. That method involves preparing a cannabinoid-infused ice cream or crème anglaise. First, a cannabinoid tincture is created by combining liquor or oil and a cannabinoid distillate, Isolate or other intended extract that includes cannabinoids, such as cannabis, THC, CBD, CBN or CBG, and heating the combination at a low heat, preferably 110- to 160-degrees Fahrenheit. Then heavy cream is combined with half of the tincture and the mixture is simmered to 160-degrees Fahrenheit for approximately 15 minutes, or until the alcohol has evaporated and is evenly infused. The mixture is removed from heat, lecithin is incorporated, and then the mixture is chilled in a refrigerator. The remainder of the cannabinoid-tincture is combined with milk and then sonicated for approximately 10 minutes to create a cannabinoid-infused milk, which is included in the preparation of a custard base, preferably a crème anglaise. The cannabinoid-infused custard base and cannabinoid-infused cream are incorporated and churned to prepare ice cream, frozen sorbet or a mixture of the two. The ice cream is spread in a rectangular container, halved and frozen for approximately 48 hours at a temperature between −25 and −40 degrees Fahrenheit. The ice cream is then cut into equal pieces of approximately 0.5×2.5×3.5 inches, placed back in the −25 and −40 degrees Fahrenheit for 12 hours, and then processed via equal 12-hour freeze and dry cycles, under a vacuum, totaling 24 hours. The freeze-dried pieces and an oxygen absorber are placed in a flexible package which is vacuum sealed for storage. The cannabinoid-infused ice cream products are shelf-stable for at least six months.

Figure 3:
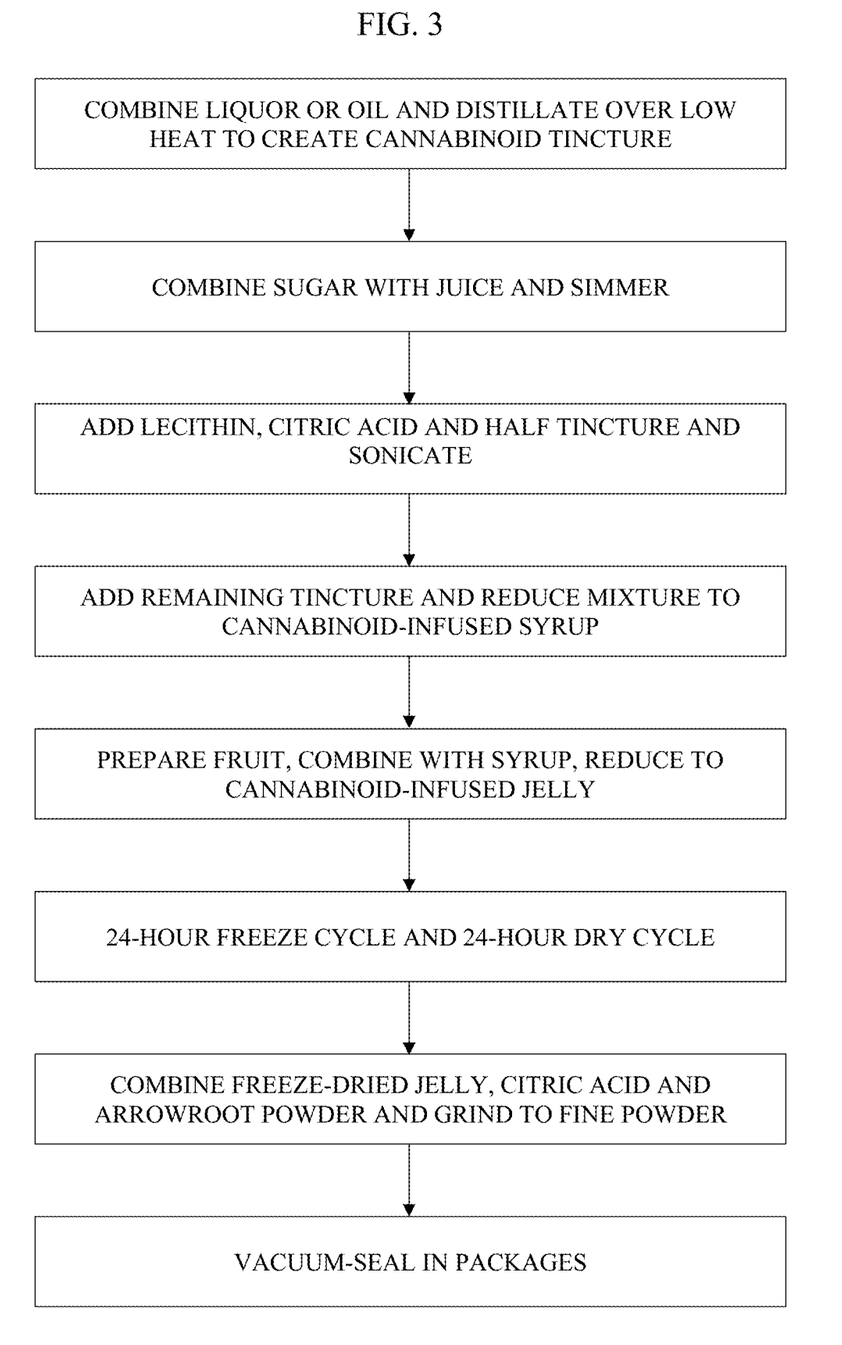
FIG. 3 is a flow chart of a third method for producing a medicinal food product according to the present disclosure.

Referring now to FIG. 3, a method for producing a cannabinoid infused drink and smoothie powder is disclosed. First, a cannabinoid tincture is prepared by combining liquor or oil with a cannabis distillate, Isolate or other intended extract that includes cannabinoids, such as cannabis, THC, CBD, CBN or CBG, and heating the combination to between approximately 110 and 160 degrees. Coconut, Monk Fruit sugar or an alternative sugar sweetener are combined with pineapple juice and simmered at approximately 200-degrees until a desired consistency and viscosity are achieved to prepare a syrup base. Lecithin, citric acid and half of the cannabinoid tincture are mixed and sonicated with the syrup for 10 minutes to create a nanoemulsion, or until the mixture runs uniform. Following that, the remainder of the cannabinoid tincture is added to the syrup which is reduced to a desired consistency to create a cannabinoid-infused syrup carrier. That carrier is refrigerated until cool then set out at room temperature for 45 minutes.

Next, fruit, vegetables and/or jam/jelly are combined with the carrier and simmered until reduced to a jelly consistency resulting in a cannabinoid-infused jelly. The cannabinoid-infused jelly is then placed on a tray and processed through a 24-hour freeze cycle followed by a 24-hour dry cycle under a vacuum to create a freeze-dried cannabinoid-infused jelly. From there, the freeze-dried jelly is combined with citric acid and arrowroot powder in a food processor and a fine powder is produced. The fine powder is divided into equal portions and placed in vacuum sealed bags along with oxygen absorbers. The cannabinoid-infused smoothie powder is shelf stable for at least 25 years.

Figure 4:
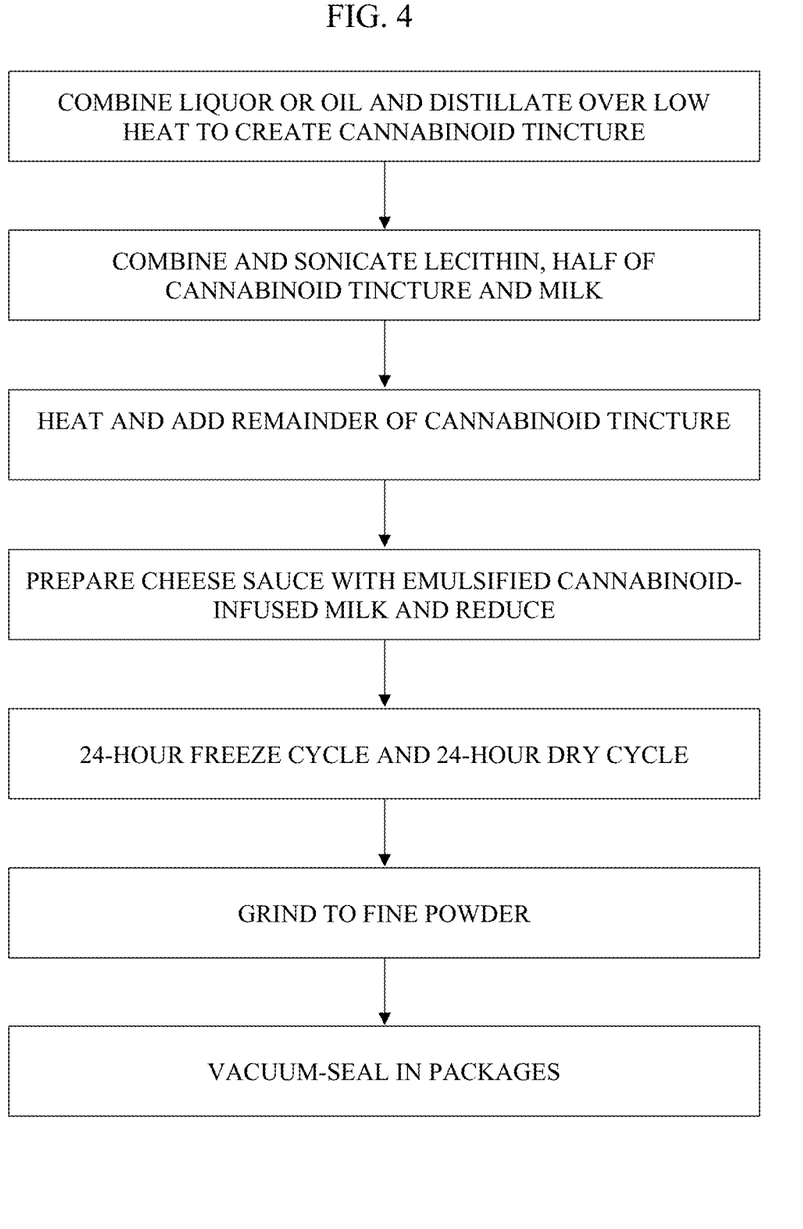
FIG. 4 is a flow chart of a fourth method for producing a medicinal food product according to the present disclosure.

Referring now to FIG. 4, there is shown a method for producing a cannabinoid-infused cheese, desert or savory sauce. The method includes producing a cannabinoid tincture by mixing and heating liquor or oil with a cannabinoid distillate, Isolate or other intended extract, that includes cannabinoids, such as cannabis, THC, CBD, CBN or CBG. Milk is then heated to approximately 110- to 160-degrees Fahrenheit, mixed with half of the cannabinoid tincture and lecithin, and sonicated until emulsified, which requires approximately 10 minutes of sonication. The mixture is then returned to heat and the remaining cannabinoid tincture is added to the mixture to create a cannabinoid-infused milk carrier. The carrier is chilled and set out at room temperature for 45 minutes and then used to create a cheese sauce, preferably by combining the carrier with a butter and flour roux, cheese, onion brulee, bay leaf and cloves. The cheese sauce is spread on a tray and processed through a freeze cycle of 24 hours followed by a dehydration cycle of 24 hours under a vacuum resulting in a freeze-dried cannabinoid infused cheese sauce. The freeze-dried cheese sauce is ground to a powder, divided into equal portions and placed in vacuum sealed bags. The cannabinoid-infused cheese powder is shelf-stable for at least 25 months.

Figure 5:
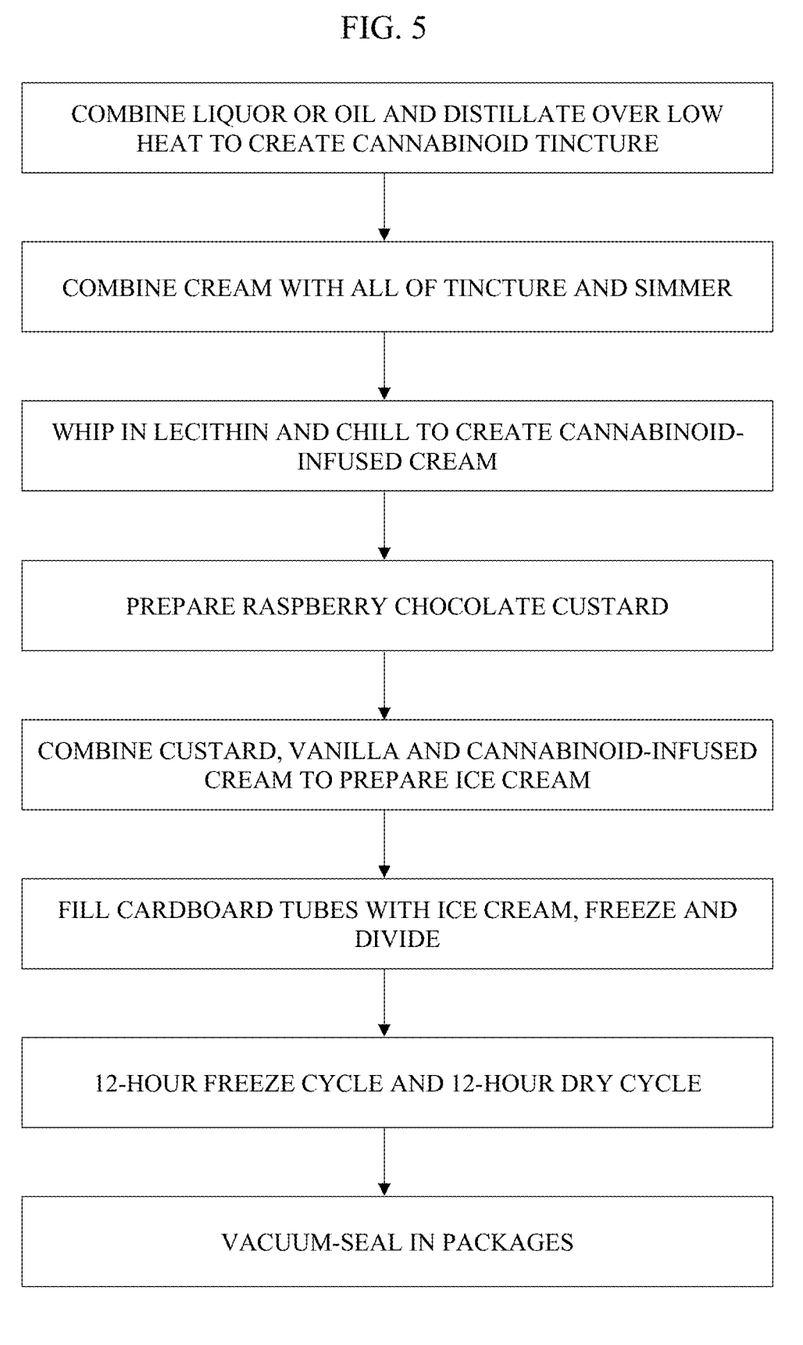
FIG. 5 is a flow chart of a fifth method for producing a medicinal food product according to the present disclosure.

FIG. 5 shows a method for producing a cannabinoid-infused coffee creamer. That method includes producing a cannabinoid tincture by combining and heating liquor or oil and a cannabinoid distillate, Isolate or other intended extract. The entirety of the tincture is combined with heavy cream and simmered at 160-degrees Fahrenheit until all alcohol has evaporated and the cream is infused, which takes approximately 15 minutes. Lecithin is then whipped into the mixture to prepare a cannabinoid-infused cream carrier. A crème anglaise is prepared with sugar, milk, salt, eggs, and a flavoring agent, such as chocolate. The crème anglaise is chilled, mixed with the cannabinoid-infused cream carrier and vanilla, and churned to create a cannabinoid-infused ice cream. The ice cream is piped into 2" cardboard tubes and frozen for at least 48 hours. Following that, the frozen coffee creamer is divided into ⅜×2-inch cylindrical portions which are processed through a 12-hour freeze cycle followed by a 12-hour dehydration cycle under a vacuum resulting in individual freeze-dried cannabinoid-infused coffee creamers. The individual portions are each placed in a flexible bag with an oxygen absorber and vacuum sealed to provide freeze-dried cannabinoid-infused coffee creamers that are shelf-stable for at least 6 months.

Referring now to FIGS. 6-11, embodiments of medicinal food products are shown. The medicinal food product 2 of FIG. 6 includes a freeze-dried medicinal food item 4 that includes a medicinal-infused food-based carrier 6 including a homogenous mixture of a first non-medicinal food base, a cannabinoid product and lecithin. There is a second food base 8 that is mixed with the cannabinoid-infused food-based carrier to create a cannabinoid-infused food item 4, which is processed through equal freeze and dehydration times under a vacuum and divided as described above through the methods of FIGS. 1-5. The food item 4 is then placed in a flexible bag 10 and vacuum sealed with an oxygen absorber to provide a freeze-dried medicinal food product that is shelf stable for an extended period of time of at least 6 months.

Figure 6:
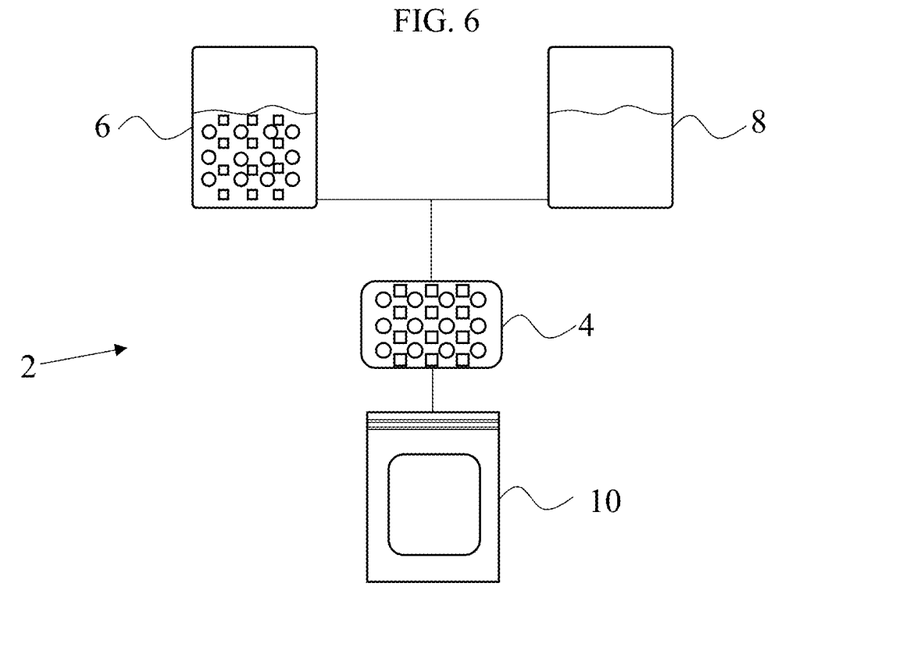
FIGS. 6 and 7 illustrate two embodiments, respectively, of medicinal food products according to the present disclosure.
Figure 8:
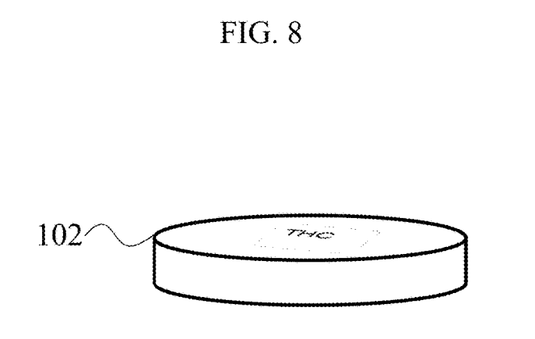
FIGS. 8-11 illustrate further embodiments of medicinal food products according to the present disclosure.
Figure 9:
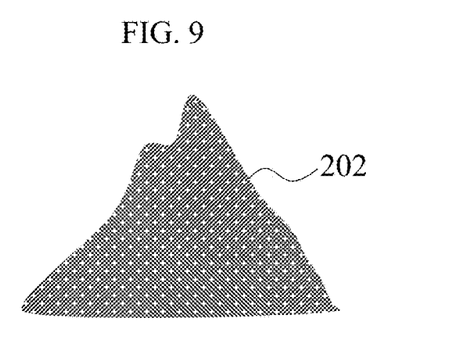
Figure 10:
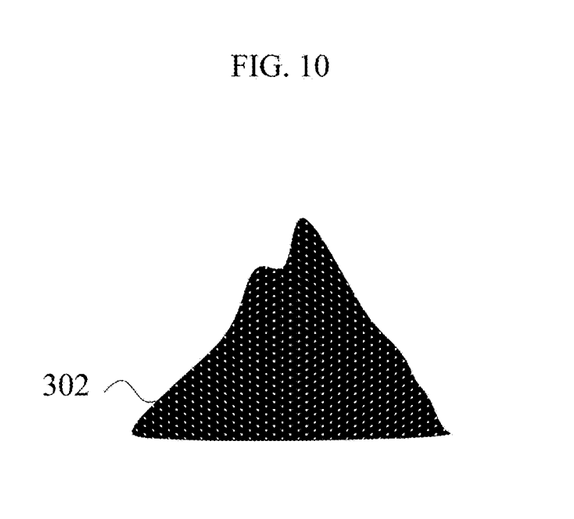

FIGS. 8-10 show specific embodiments of medicinal food products according to the product shown in FIG. 6, including a coffee creamer 102 shown in FIG. 8 which is produced according to the method steps of FIG. 5. The creamer includes a THC marking to denote that it includes Tetrahydrocannabinol. A cheese sauce powder 202 is shown in FIG. 9 which is produced according to the method steps of FIG. 4, and a drink/smoothie powder 302 is shown in FIG. 10 which is produced according to the method steps of FIG. 3.

Figure 7:
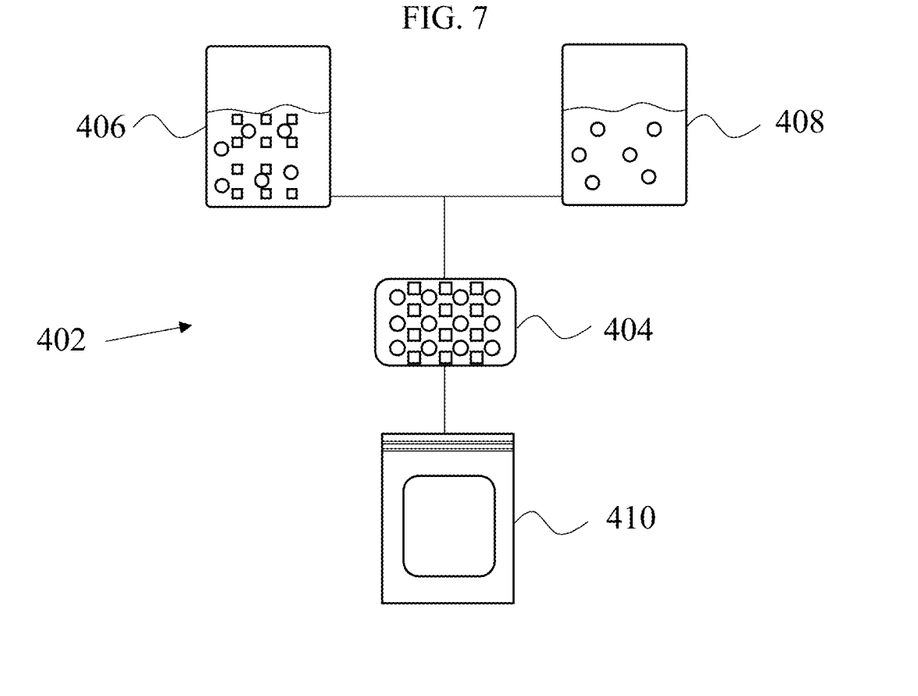
Figure 11:
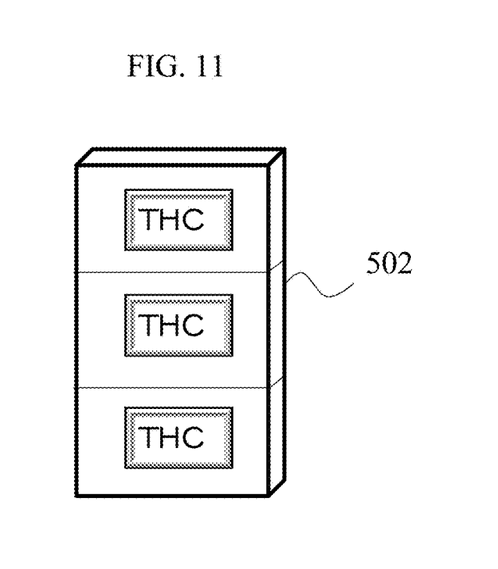

Another embodiment of a medicinal food product 402 is shown in FIG. 7. That product is a freeze-dried medicinal food item 404 that includes a first medicinal-infused food-based carrier 406 combined with a second medicinal-infused food-based carrier 408. The first carrier includes a homogenous mixture of a first non-medicinal food base, a cannabinoid product and lecithin, and the second carrier includes a homogenous mixture of a second non-medicinal food base and a cannabinoid product. The product is freeze-dried and placed in a vacuum sealed flexible bag 410. FIG. 11 shows a cannabinoid-infused ice cream bar 502 which is produced according to the method steps of FIG. 2. As with the creamer, the ice cream bar includes THC markings to denote that it includes Tetrahydrocannabinol.

Although the above description includes references to particular embodiments, it is to be understood that these embodiments are merely illustrative of the principles and applications of the present disclosure. It is therefore to be understood that numerous modifications may be made to the illustrative embodiments and that other arrangements may be devised and employed without departing from the spirit and scope of the present disclosure.

What is claimed is:

1. A method for producing a medicinal food product comprising the steps of:
    a. homogenously mixing a first food product with cannabis and lecithin to prepare a cannabis/first food product/lecithin mixture;
    b. heating the cannabis/first food product/lecithin mixture to 100° F.-200° F.;
    c. sonicating the cannabis/first food product/lecithin mixture;
    d. mixing the cannabis/first food product/lecithin mixture with a second food product to create a cannabis/first food product/lecithin/second food product;
    e. freezing the cannabis/first food product/lecithin/second food product for 10 hours-48 hours;
    f. dehydrating the cannabis/first food product/lecithin/second food product for 10 hours-48 hours;
    g. dividing the cannabis/first food product/lecithin/second food product into containers; and
    h. vacuum sealing the containers with oxygen absorbers to produce containers of cannabis/first food product/lecithin/second food product.

2. A method for producing a medicinal food product as defined in claim 1, wherein said containers are flexible.

3. A method for producing a medicinal food product as defined in claim 1, wherein said first food product comprises heavy cream.

4. A method for producing a medicinal food product as defined in claim 3, wherein said second food product comprises one of a custard base and crème-anglaise to produce containers of a freeze-dried cannabis-infused ice cream product.

5. A method for producing a medicinal food product as defined in claim 3, wherein said second food product comprises a crème-anglaise to produce containers of a freeze-dried cannabis-infused coffee creamer product.

6. A method for producing a medicinal food product as defined in claim 1, wherein said first food product comprises syrup.

7. A method for producing a medicinal food product as defined in claim 6, said second food product comprises at least one of a fruit, vegetable and a preserve to produce containers of a freeze-dried cannabis-infused powdered drink product.

8. A method for producing a medicinal food product as defined in claim 1, wherein said first food product comprises milk.

9. A method for producing a medicinal food product as defined in claim 8, wherein said second food product comprises cheese to produce containers of a freeze-dried cannabis-infused cheese product.

* * * * *